(12) United States Patent
Yao

(10) Patent No.: US 8,216,617 B2
(45) Date of Patent: Jul. 10, 2012

(54) TABLET COMPRISING NATURAL ALLICIN AND METHOD FOR PRODUCING THE SAME

(76) Inventor: Ying Yao, Hangzhou (CN)

( * ) Notice: Subject to any disclaimer, the term of this patent is extended or adjusted under 35 U.S.C. 154(b) by 0 days.

(21) Appl. No.: 12/943,034

(22) Filed: Nov. 10, 2010

(65) Prior Publication Data

US 2011/0052568 A1    Mar. 3, 2011

Related U.S. Application Data

(63) Continuation of application No. PCT/CN2009/072602, filed on Jul. 2, 2009.

(30) Foreign Application Priority Data

Jul. 3, 2008 (CN) .......................... 2008 1 0062759

(51) Int. Cl.
*A61K 36/00* (2006.01)
*A61K 31/36* (2006.01)
*A61K 36/8962* (2006.01)
*A61K 39/395* (2006.01)

(52) U.S. Cl. .................. 424/725; 424/754; 424/130.1
(58) Field of Classification Search .................. None
See application file for complete search history.

(56) References Cited

U.S. PATENT DOCUMENTS

2008/0275110 A1 * 11/2008 Ono et al. .................. 514/464

FOREIGN PATENT DOCUMENTS

| JP | 58157722 A | * | 9/1983 |
| JP | 2008105998 A | * | 5/2008 |

OTHER PUBLICATIONS

Kim et al, Antioxidant and anti-inflammatory activities of the mung bean, Cosmetics & Toiletries, (1998), 113 (8), 71-74.*
Francis et al, Constituents in Easter lily flowers with medicinal activity, Life Science (2004), 76 (6): 671-683.*

* cited by examiner

*Primary Examiner* — Qiuwen Mi
(74) *Attorney, Agent, or Firm* — Matthias Scholl P.C.; Matthias Scholl

(57) ABSTRACT

A tablet including 1,000 weight parts of 21-90% natural allicin powder, 10-30 weight parts of 50-95% sesamin, 10-30 weight parts of 50-95% IgY or IgG, and a release agent. The allicin content of the tablet is 200-800 mg/g. The allicin tablet has high allicin content and capability of anti-bacteria and anti-inflammation, and can be administered based on the body weight of an animal in need thereof but causes no side effects. A method for producing the allicin tablet by mixing and uniformly stirring starch, garlic powder, and natural allicin powder to yield a mixture, adding the natural sesamin, Ig Y or Ig G, and magnesium stearate to the mixture, uniformly stirring, and tabletting.

15 Claims, 2 Drawing Sheets

TABLET COMPRISING NATURAL ALLICIN AND METHOD FOR PRODUCING THE SAME

CROSS-REFERENCE TO RELATED APPLICATIONS

This application is a continuation of International Patent Application No. PCT/CN2009/072602 with an international filing date of Jul. 2, 2009, designating the United States, now pending, and further claims priority benefits to Chinese Patent Application No. 200810062759.7 filed Jul. 3, 2008. The contents of all of the aforementioned applications, including any intervening amendments thereto, are incorporated herein by reference.

BACKGROUND OF THE INVENTION

1. Field of the Invention

The invention relates to a plant extract preparation, and more particularly to a tablet comprising natural allicin and a method for producing the same.

2. Description of the Related Art

Natural allicin is a mixture mainly composed of diallyl-trisulfide, diallyl disulfide, diallyl-thiosulfinate, ajoene, and vinyldithiins. Generally, the allicin content refers to the total amount of the above mentioned five active ingredients. Natural allicin is extracted from garlic and plays a role something like broad-spectrum antibiotics and a vascular cleaner or protector. Thus, it exhibits strong medicinal functions.

As a vascular protector, a daily intake of between 5 and 80 mg of allicin is enough for a grownup. However, if functioning as broad-spectrum antibiotics to kill infectious viruses and bacteria, the administered allicin must be large, for example, exceeding 200 mg per time per 10 kg of body weight. Conventional allicin tablets contain a limited dose of allicin, for example, 20 mg or 25 mg of allicin per piece, and the dosage is 2-3 times per day with 2-6 pieces per time. Many practices have proved the fact that the prevention and treatment effect on worse diseases caused by viruses or bacteria is poor when the intake amount does not exceed 120 mg each time for people. Obviously, the dosage amount is not enough for preventing and treating diseases. However, administering a large amount of allicin one time is harmful to body. Experiments showed that a large amount of allicin collapsed the heart of mice or rabbits. If a human was administered with 700 mg or more of natural allicin (i.e., 1,000 mg of a 70% concentrated natural allicin extract) alone, the chest and abdomen swelled and made him uncomfortable. The more allicin was ingested, the larger the swelling that was observed. Thus, it is urgent to develop an allicin tablet which can be administered largely within an effective dose but causes no harm to human body.

SUMMARY OF THE INVENTION

In view of the above-described problems, it is one objective of the invention to provide a tablet that comprises high content of allicin, can be administered according to the body weight of a human in need thereof, involves no artificial chemicals, and exhibits good effect on anti-bacteria, anti-inflammation, and anti-virus.

To achieve the above objectives, in accordance with one embodiment of the invention, there is provided a tablet comprising 1,000 weight parts of 21-90% natural allicin powder, 10-30 weight parts of 50-95% sesamin, 10-30 weight parts of 50-95% IgY or IgG, and a release agent, the allicin content of the tablet being 200-800 mg/g.

In accordance with another embodiment of the invention, there is provided a tablet comprising 1,000 weight parts of 62-80% natural allicin powder, 20-80 weight parts of 50-95% sesamin, 20-80 weight parts of 50-95% IgY or IgG, 38-460 weight parts of starch, 100-1500 weight parts of garlic powder, and a release agent, the allicin content of the tablet being 200-600 mg/g.

In a class of this embodiment, the release agent is magnesium stearate.

In a class of this embodiment, the tablet comprises 1,000 weight parts of 62-80% natural allicin powder, 20-80 weight parts of 50-95% sesamin, 20-80 weight parts of 50-95% IgY or IgG, 340-460 weight parts of starch, 550-1500 weight parts of garlic powder, and 6 weight parts of magnesium stearate, and the allicin content of the tablet is 200-400 mg/g.

In a class of this embodiment, the tablet comprises 1,000 weight parts of 62-80% natural allicin powder, 20-70 weight parts of 50-95% sesamin, 20-70 weight parts of 50-95% IgY or IgG, 80-460 weight parts of starch, 460-550 weight parts of garlic powder, and 4 weight parts of magnesium stearate, and the allicin content of the tablet is 300-500 mg/g.

In a class of this embodiment, the tablet comprises 1,000 weight parts of 62-80% natural allicin powder, 20-50 weight parts of 50-95% sesamin, 20-50 weight parts of 50-95% IgY or IgG, 38-80 weight parts of starch, 200-460 weight parts of garlic powder, and 3 weight parts of magnesium stearate, and the allicin content of the tablet is 400-600 mg/g.

In a class of this embodiment, the tablet comprises 1,000 weight parts of 62-80% natural allicin powder, 20-40 weight parts of 50-95% sesamin, 20-40 weight parts of 50-95% IgY or IgG, 38 weight parts of starch, 100-190 weight parts of garlic powder, 2 weight parts of magnesium stearate, and 10-100 weight parts of a cool or cold food additive, and the allicin content of the tablet is 400-600 mg/g.

In a class of this embodiment, the cool or cold food additive is corn, wheat, barley, buckwheat, coix Seed, millet, mung bean, green bean sprouts, bitter melon, white fungus, seaweed, lettuce, aloe vera, white radish, asparagus, celery, water bamboo, coriander, white gourd, lily, towel gourd, spinach, amaranth, water spinach, fern, dandelion, clover blossom, sugar beet, sweet potato, konjak, water pack, eggplant, daylily, mushroom, cucumber, watermelon, melon, banana, rape, water chestnuts, water chestnut meat, lotus root, lotus seed, nelumbinis embryo, green tea, chrysanthemum, honeysuckle, apple, pear, orange, persimmon, hylocereusundatus fruit, star fruit, mangosteen, strawberries, loquat, cherry tomato, medlar, grapefruit, kiwi fruit, soft-shelled turtle, turtle, duck, frog, jellyfish, snail, crab, clam, mussel, snakehead, snail, snake, or a mixture thereof, among which an extract from mungbean sprout or lily is preferable. The extract content is 40-95%.

In a class of this embodiment, the allicin content of the natural allicin power is 65-75%.

The preparation method of the cool or cold food additive comprises grinding a raw material, extracting with liquor, filtering, removing residue and alcohol, and freeze-drying to yield a powder or powder block.

The 21-90% natural allicin powder was purchased from Hangzhou Shenzhou Earth Ecology Culture Institute.

As far as traditional Chinese medicine is concerned, garlic is hot-natured, so the natural allicin tablet is particularly suitable for humans with a cool- or cold-natured body. For humans with a hot-natured body, the above-mentioned cool or cold food additive can be added to the tablet. If the tablet comprises no cool or cold food additive, humans with a hot-natured body can eat sufficient cool or cold food when administering the tablet.

A method for producing the allicin tablet comprises mixing the materials, uniformly stirring, and tabletting.

Another method for producing the allicin tablet comprises mixing and uniformly stirring starch, garlic powder, and natural allicin powder, adding natural sesamin, Ig Y or Ig G, the release agent, and the cool or cold food additive, uniformly stirring, and tabletting.

The release agent ensures the molds to be easily released and not sticky in the process of tabletting, the addition amount thereof is not related to the allicin content.

The prepared allicin tablet is 1,000 mg/piece (1 g/piece), with allicin content of 200-700 mg/piece. The tablet can be administered according to body weight, i.e., one piece/10 kg body weight, 2-3 times per day.

The allicin tablet has high content of allicin. Clinical applications have shown that for a seriously-ill patient, natural allicin can weaken the diseases but the administered dosage must be large. Generally, the dosage is 200-700 mg/10 kg body weight. For example, for a person with weight body of 50 kg, the oral dosage of natural allicin should be 1,000-3,500 mg per time, and 2-3 times a day. The allicin tablet can effectively kill inflammation, viruses, and infectious bacteria, without side effects and drug resistance. Thus, it is very safe and moderate.

Conventional Chinese medicine pays good attention to the compatibility of different active ingredients. Pure allicin extracted from garlic is separated from other components therein. Thus, when administering to human body alone, people fall into an unbalanced and uncoordinated state. The purer in concentration or higher in quantity of the allicin, the worse the balance and the coordination. However, after mixed with a garlic powder, the allicin seems to recombine with other components of the garlic. High content of allicin together with other trace elements and nutritious components protects human body harmoniously and effectively.

Single allicin can prevent and weaken diseases caused by nearly all the bacteria or virus, but a few of cases showed some of bacteria or virus cannot be rooted up if intaking allicin singly. The addition of a little sesamin can reach the effect and the treatment effect comes much sooner. If a little IgG or IgY is added, the effect is much better. The allicin, sesamin, and IgG or IgY are compatible with each other and can be administered largely within an effective dose but cause no side effects to human body. The ingredients that are admixed with allicin and the proportions thereof are critical to ensuring optimal health benefits without side effects. The invention of the allicin tablet frees people from the over-dependence on chemical antibiotics as soon as possible.

BRIEF DESCRIPTION OF THE DRAWINGS

The invention is described herein below with reference to accompanying drawings, in which.

DETAILED DESCRIPTION OF THE EMBODIMENTS

To further illustrate the invention, experiments detailing an allicin tablet, a preparation method, and the use thereof are described below. It should be noted that the following examples are intended to describe and not to limit the invention.

The 30-90% natural allicin powder used in following examples is produced and sold by Hangzhou Shenzhou Earth Ecology Culture Institute with a concentration of 30-90%. A sample is examined by Zhejiang University and Zhejiang Food Quality Supervision and Inspection Station. The examination results are listed in Tables 1-3.

TABLE 1

Sensory evaluation of the natural allicin powder produced by Hangzhou Shenzhou Earth Ecology Culture Institute

| Items | Results |
|---|---|
| Appearance | Light yellow solid powder |
| Smell | A little garlic smell, no odour |
| Flavor | A little garlic taste, no odour |
| Degree of fineness | 80 mesh |

Due to different garlic origin or production time, the natural allicin powder is milk white, light yellow, or brown.

TABLE 2

Sanitary evaluation of the natural allicin powder produced by Hangzhou Shenzhou Earth Ecology Culture Institute

| Items | Unit | Standard value | Measured value | Results |
|---|---|---|---|---|
| Negative deviation of net content | % | $\leq 9$ | 0 | Satisfied |
| Impurity | % | / | 0.05 | Satisfied |
| Moisture | % | <9 | 3.26 | Satisfied |
| Ash | % | $\leq 6$ | 2.66 | Satisfied |
| Heavy metal (Hg + Pb) | mg/kg | $\leq 5.0$ | 1.03 | Satisfied |
| CFU | cfu/g | <30000 | <10 | Satisfied |
| E.coli | MPN/100 g | <90 | <30 | Satisfied |
| Mould | cfu/g | <25 | <10 | Satisfied |
| Yeast | cfu/g | <25 | <10 | Satisfied |
| Pathogen | / | Prohibited | Not found | Satisfied |

TABLE 3

Content measurement of diallyltrisulfide($C_6H_{10}S_3$) of the natural allicin powder produced by Hangzhou Shenzhou Earth Ecology Culture Institute

| Item | Sample dissolution rate | Allicin content in sample solution | Allicin content in sample solid |
|---|---|---|---|
| Content of allicin | 66% | 66.5371% | 43.91% |

Figure 1:
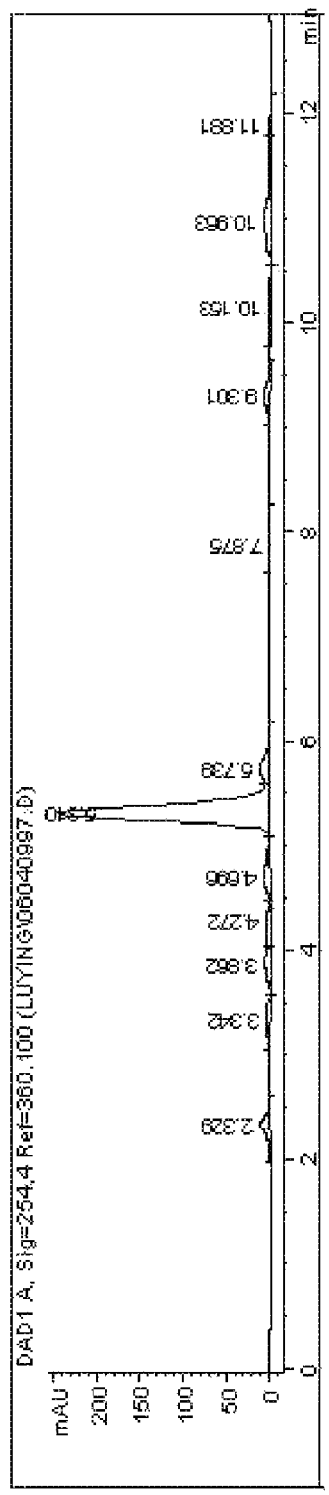
FIGS. 1-4 show HPLC (High performance liquid chromatography) traces of an allicin powder according to one embodiment of the invention.
Figure 2:
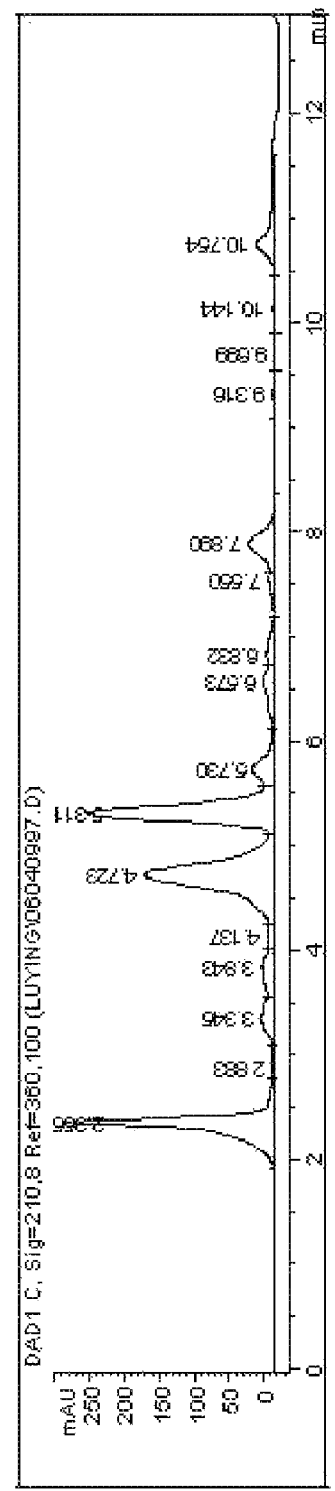
Figure 3:
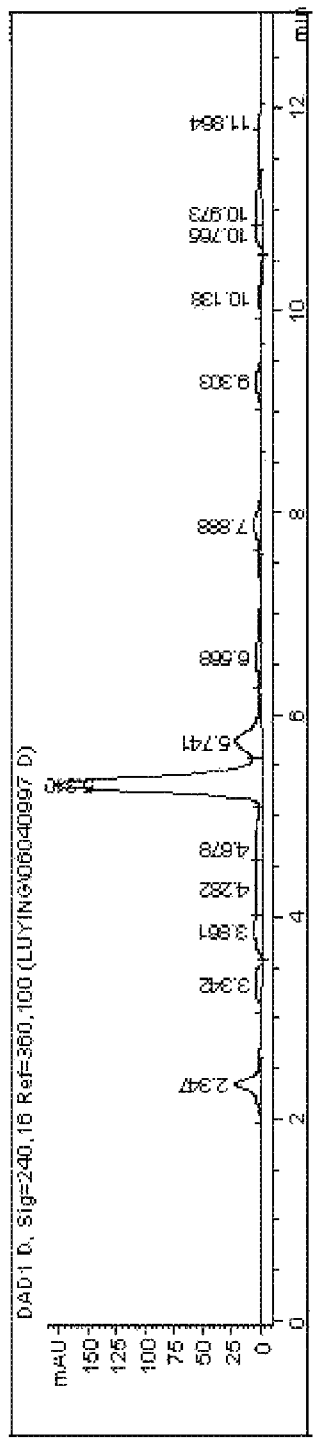
Figure 4:
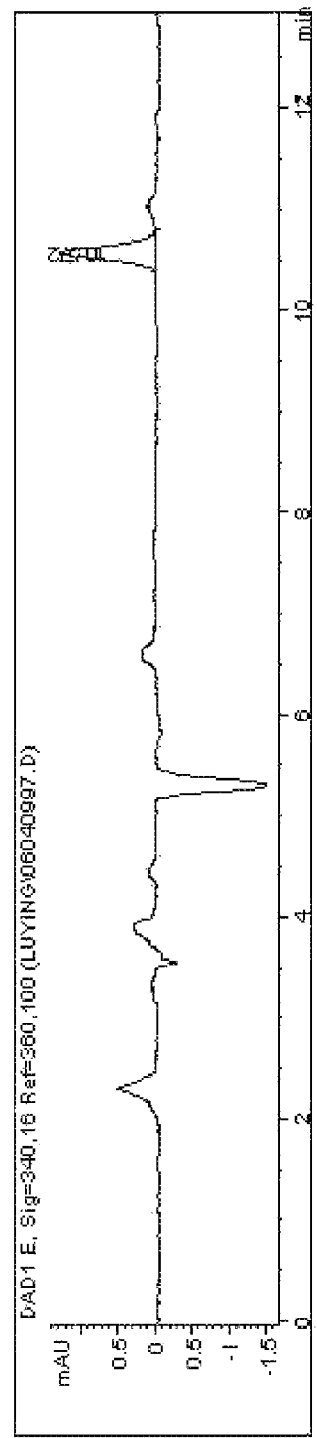

The measurement result of diallyltrisulfide is shown in FIGS. 1-4 in which the peak value represents the content of $C_6H_{10}S_3$.

Example 1

500 g of 65-70% natural allicin powder, 230 g of starch, and 230 of a garlic powder were mixed and stirred to yield a uniform mixture. To the uniform mixture, 20 g of 65% natural sesamin, 20 g of 80% IgG, and 2 g of magnesium stearate were added, stirred uniformly, and tabletted. The resultant mixture was 1,002 g in weight and tabletted into 1,002 pieces. Each piece was 1 g, with allicin content exceeding 300 mg, generally between 324 and 350 mg.

Example 2

1,000 g of 65-70% natural allicin powder, 20 g of 65% natural sesamin, 20 g of 80% IgY, and 2 g of magnesium stearate were mixed, stirred uniformly, and tabletted. The resultant mixture was 1,042 g in weight and tabletted into 1,042 pieces. Each piece was 1 g, with allicin content exceeding 600 mg, generally between 634 and 685 mg.

Example 3

1,000 g of 65-70% natural allicin powder, 350 g of starch, and 1,500 of a garlic powder were mixed and stirred to yield a uniform mixture. To the uniform mixture, 60 g of 70% natural sesamin, 60 g of 80% IgY, and 6 g of magnesium stearate were added, stirred uniformly, and tabletted. The resultant mixture was 2,976 g in weight and tabletted into 2,976 pieces. Each piece was 1 g, with allicin content exceeding 200 mg, generally between 218 and 235 mg.

Example 4

1,000 g of 65-70% natural allicin powder, 450 g of starch, and 550 of a garlic powder were mixed and stirred to yield a uniform mixture. To the uniform mixture, 40 g of 70% natural sesamin, 40 g of 80% IgY, and 4 g of magnesium stearate were added, stirred uniformly, and tabletted. The resultant mixture was 2,084 g in weight and tabletted into 2,084 pieces. Each piece was 1 g, with allicin content exceeding 300 mg, generally between 312 and 336 mg.

Example 5

1,000 g of 65-70% natural allicin powder, 50 g of starch, and 450 of a garlic powder were mixed and stirred to yield a uniform mixture. To the uniform mixture, 30 g of 70% natural sesamin, 30 g of 80% IgY, and 3 g of magnesium stearate were added, stirred uniformly, and tabletted. The resultant mixture was 1,563 g in weight and tabletted into 1,563 pieces. Each piece was 1 g, with allicin content exceeding 400 mg, generally between 416 and 448 mg.

Example 6

1,000 g of 65-70% natural allicin powder, 38 g of starch, and 160 of a garlic powder were mixed and stirred to yield a uniform mixture. To the uniform mixture, 20 g of 70% natural sesamin, 20 g of 80% IgY, 40 g of a 70% cool food additive, and 2 g of magnesium stearate were added, stirred uniformly, and tabletted. The resultant mixture was 1,280 g in weight and tabletted into 1,280 pieces. Each piece was 1 g, with allicin content exceeding 500 mg, generally between 508 and 547 mg.

Example 7

18 white rabbits (all were 1 kg in body weight) suffering from bacillary dysentery were divided into three groups (Group A, B, and C) randomly. The rabbits were treated separately. The treatment method and the results are shown in Table 4.

TABLE 4

| Group | Treatment | Results |
|---|---|---|
| A | 100 mg of an allicin tablet with allicin content of between 30 and 70 mg was administered, a piece one time, three times per day. | Diarrhea disappeared on the treatment day. After administration on the next day, all the six rabbits recovered completely. |
| B | 100 mg of an allicin tablet with allicin content less than 30 mg was administered, a piece one time, three times per day. | Diarrhea weakened on the treatment day. On the next day, diarrhea disappeared. On the $3^{rd}$ day, all the six rabbits recovered completely. |
| C | No allicin was administered. | All the six rabbits died. |

Example 8

Eight German shepherd puppies suffered from plague, two of which were treated with injections and medicine without allicin, finally died. The rest six were at their last gasp and could not stand up. The allicin tablet of the invention was administered to the six puppies, three times a day. On the first administration day, the puppies stood up, walked around, and took food. On the $3^{rd}$ day, the puppies recovered completely, with good appetite and walked smoothly. In the process of treating the six puppies, no injections and medicine involved.

Example 9

The following are clinical cases about the treatment effect of the natural allicin tablet on patients.

1. The natural allicin tablet was administered to nine patients catching a cold. After an hour, cold symptoms were alleviated. After three times' administration, the patients recovered completely.

2. A nephritis patient had high content of urine protein. After 15 days' administration of the natural allicin tablet, the urine protein content decreased greatly and fell into the normal range.

3. A patient almost recovered from leukemia after hospital treatment. However, the disease relapsed soon and worsened. He had a fever everyday and severe oral ulcer. The natural allicin tablet was administered to the patient. Three days later, his body temperature was back to normal and the oral ulcer disappeared.

4. A lymphoma patient experiencing chemotherapy had severe oral ulcer and could not eat. Nothing but the natural allicin tablet was administered to the patient. Four days later, the oral ulcer disappeared.

5. A nasopharyngeal carcinoma patient experiencing chemotherapy had severe oral ulcer. Chinese medicine and anti-inflammatory drugs were tried but had no effect. The natural allicin tablet was administered to the patient. Four days later, the oral ulcer disappeared.

6. A liver and intestinal cancer patient was administered with eight bottles of the allicin tablet of the invention and twelve bottles of common allicin tablet. The disease weakened with passing day and the liver ache almost disappeared.

7. A patient whose liver ached sometimes for several days was administered with the allicin tablet of the invention. Two days later, the ache disappeared.

8. A patient had yellow and smellyleucorrhea. Many anti-inflammatory and anti-bacterial drugs were tried but had no effect. The natural allicin tablet was administered to the patient. Several days later, the inflammation disappeared.

9. Two patients suffering from stomach disease was administered with the allicin tablet of the invention. Several days later, the disease was alleviated.

10. A diarrhea patient was administered with the allicin tablet of the invention. Several times later, the diarrhea disappeared.

11. Seven patients suffering from toothache which resulted in headache was administered with the allicin tablet of the invention. Several times later, the aches disappeared.

12. Two patients suffering from urinary tract infection were administered with the allicin tablet of the invention. Three times later, the disease disappeared.

13. Two patients having nasal obstruction were administered with the allicin tablet of the invention. Three times later, the disease disappeared.

14. A patient suffering from prostatitis was administered with the allicin tablet of the invention. One week later, the disease weakened.

15. A patient suffering from an inflamed and aching tonsil with fever was administered with the allicin tablet of the invention. Half an hour later, the disease weakened. Four hours later, the allicin tablet was administered again. Soon, the fever and inflammation disappeared.

16. A patient suffering from high fever was administered with the allicin tablet of the invention thrice within 15 hrs. Gradually, the fever disappeared.

17. Two girls suffered from high fever, oral and hand ulcer. They cried all the time and had no appetite. The allicin tablet of the invention was administered. After an hour, the girls calmed down and had appetite. In the following two days, some medicine and the tablet were administered and all the symptoms disappeared soon.

These clinical cases show that the allicin tablet has capability of anti-bacteria and anti-inflammation. However, in use, the dosage should be large. In contrast to the allicin tablets in the prior art, the tablet has the characteristic of the highest allicin content per piece, the largest dosage administered safely and no side effects.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A tablet comprising 1,000 weight parts of 21-90% allicin powder, 10-30 weight parts of 50-95% sesamin, 10-30 weight parts of 50-95% IgY or IgG, and a release agent, the allicin content of said tablet being 200-800 mg/g.

2. The tablet of claim 1, wherein the allicin content of said allicin powder is 65-75%.

3. The tablet of claim 1, wherein said release agent is magnesium stearate.

4. The tablet of claim 1, wherein said tablet weighs 1 g.

5. A tablet comprising 1,000 weight parts of 62-80% allicin powder, 20-80 weight parts of 50-95% sesamin, 20-80 weight parts of 50-95% IgY or IgG, 38-460 weight parts of starch, 100-1500 weight parts of garlic powder, and a release agent, the allicin content of said tablet being 200-600 mg/g.

6. The tablet of claim 5, wherein the allicin content of said allicin powder is 65-75%.

7. The tablet of claim 5, wherein said release agent is magnesium stearate.

8. The tablet of claim 5, wherein said tablet weighs 1 g.

9. The tablet of claim 7, wherein said tablet comprises 1,000 weight parts of 62-80% allicin powder, 20-80 weight parts of 50-95% sesamin, 20-80 weight parts of 50-95% IgY or IgG, 340-460 weight parts of starch, 550-1500 weight parts of garlic powder, and 6 weight parts of magnesium stearate, and the allicin content of said tablet is 200-400 mg/g.

10. The tablet of claim 7, wherein said tablet comprises 1,000 weight parts of 62-80% allicin powder, 20-70 weight parts of 50-95% sesamin, 20-70 weight parts of 50-95% IgY or IgG, 80-460 weight parts of starch, 460-550 weight parts of garlic powder, and 4 weight parts of magnesium stearate, and the allicin content of said tablet is 300-500 mg/g.

11. The tablet of claim 7, wherein said tablet comprises 1,000 weight parts of 62-80% allicin powder, 20-50 weight parts of 50-95% sesamin, 20-50 weight parts of 50-95% IgY or IgG, 38-80 weight parts of starch, 200-460 weight parts of garlic powder, and 3 weight parts of magnesium stearate, and the allicin content of said tablet is 400-600 mg/g.

12. A tablet comprising 1,000 weight parts of 62-80% allicin powder, 20-40 weight parts of 50-95% sesamin, 20-40 weight parts of 50-95% IgY or IgG, 38 weight parts of starch, 100-190 weight parts of garlic powder, 2 weight parts of magnesium stearate, and 10-100 weight parts of a cool or cold food additive, wherein the allicin content of said tablet is 400-600 mg/g, and said cool or cold food additive is an extract from lilies.

13. The method for producing said tablet of claim 7 comprises mixing and uniformly stirring said starch, said garlic powder, and said allicin powder to yield a mixture, adding said sesamin, Ig Y or Ig G, and said magnesium stearate to said mixture, uniformly stirring, and tabletting.

14. The method of claim 13, further comprising adding a cool or cold food additive to said mixture.

15. The tablet of claim 14, wherein said cool or cold food additive is an extract from mungbean sprout or lily.

* * * * *